United States Patent [19]

Petersen et al.

[11] 4,312,859

[45] Jan. 26, 1982

[54] SISOMICIN DERIVATIVES, PROCESSES FOR THEIR PRODUCTION AND THEIR MEDICINAL USE

[75] Inventors: Uwe Petersen, Leverkusen; Karl G. Metzger, Wuppertal; Hans-Joachim Zeiler, Velbert; Peter Stadler, Haan; Eckart Voss, Cologne, all of Fed. Rep. of Germany

[73] Assignee: Bayer Aktiengesellschaft, Leverkusen, Fed. Rep. of Germany

[21] Appl. No.: 147,908

[22] Filed: May 8, 1980

[30] Foreign Application Priority Data

May 30, 1979 [DE] Fed. Rep. of Germany ....... 2921973

[51] Int. Cl.³ .................... A61K 31/71; C07H 15/22
[52] U.S. Cl. .................. 424/180; 536/17 R
[58] Field of Search ................. 536/17 R; 424/180

[56] References Cited

U.S. PATENT DOCUMENTS 3,925,354  12/1975  Umezawa et al. ............. 536/17 R
3,965,089   6/1976  Umezawa et al. ............. 536/17 R
4,104,372   8/1978  Umezawa et al. ............. 536/17 R
4,117,221   9/1978  Daniels ........................ 536/17 R Primary Examiner—Johnnie R. Brown
Attorney, Agent, or Firm—Sprung, Felfe, Horn, Lynch & Kramer

[57] ABSTRACT

The invention relates to sesomycin derivatives of Formula I, infra as well as processes for preparing said sisomycin derivatives. Also included in the invention are compositions containing said sisomycin derivatives and methods for the use of said compounds and compositions. The sisomycon derivatives are useful as antibacterial agents of broad activity and reduced side effects.

18 Claims, No Drawings

SISOMICIN DERIVATIVES, PROCESSES FOR THEIR PRODUCTION AND THEIR MEDICINAL USE

The present invention relates to new sisomicin derivatives, to processes for their production and to their use as medicaments.

Sisomicin is an antibacterially active compound of the group of aminoglycoside antibiotics.

Aminoglycoside antibiotics are important substances for effectively combating bacterial infections. However, in many cases the occurrence of resistant germs reduces their broad applicability; moreover, side effects such as ototoxicity and nephrotoxicity, can occur. In some cases it is possible to remove these disadvantages by forming derivatives.

According to the present invention there are provided compounds which are sismicin derivatives of the formula

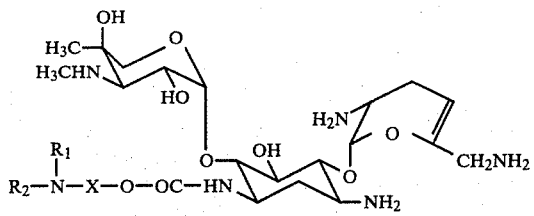

of a salt thereof,
in which
X denotes a straight-chain, branched or cyclic saturated or unsaturated aliphatic radical with 2 to 10 carbon atoms,
$R_1$ denotes a hydrogen atom or a $C_1$ to $C_4$ alkyl or benzyl radical and
$R_2$ denotes a radical of the formula

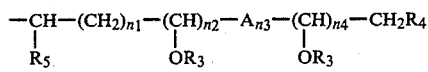

in which
A denotes

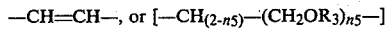

$R_3$ denotes a hydrogen atom or a triarylmethyl, alkyl or acyl radical, or 2 radicals $R_3$ together denote an alkylidene radical,
$R_4$ denotes a hydrogen atom or a $OR_3$ group in which $R_3$ has the above-mentioned meaning,
$R_5$ denotes a hydrogen atom or a $C_1$ to $C_4$ alkyl group which is optionally substituted by 1 to 3 hydroxyl groups,
$n_1$ is 0, 1, 2 or 3,
$n_2$ is 0, 1, 2, 3, 4 or 5 and
$n_3$, $n_4$ and $n_5$ independently of one another are 0, 1 or 2,
the sum of $n_1$, $n_2$, $n_3$ and $n_4$ is 1, 2, 3, 4 or 5 and the total number of $OR_3$ groups is 1 to 6. The compounds of the present invention may avoid the disadvantages mentioned for aminoglycoside antibiotics to a particularly high degree.

Preferably, X denotes a $C_2$ to $C_6$ alkylene radical and $R_1$ denotes a hydrogen atom.

$R_3$, when alkyl, is preferably $C_1$ to $C_4$-alkyl and, when acyl, is preferably $C_2$ to $C_4$ alkylcarbonyl, formyl or benzoyl. The alkylidene formed by 2 radicals $R_3$ is preferably $C_1$ to $C_6$ alkylidene. $R_3$, when triarylmethyl, is preferably triphenylmethyl.

Among the new sisomicin derivative salts of the invention those salts that are pharmaceutically acceptable are particularly important and are preferred.

The compounds of formula (I) and their pharmaceutically acceptable salts according to the invention display powerful antibacterial properties against a large number of germs and an exceptionally good tolerance. A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Examples of suitable radicals $R_2$ are straight-chain polyhydroxyalkyl radicals, such as 2,3-dihydroxypropyl, 2,3,4-trihydroxybutyl, 2,3,4,5-tetrahydroxypentyl, 2,3,4,5,6-pentahydroxyhexyl, 3,4-dihydroxybutyl, 3,4,5-trihydroxypentyl, 3,4,5,6-tetrahydroxyhexyl, 4,5-dihydroxypentyl, 4,5,6-trihydroxyhexyl, 4,5-dihydroxyhexyl, 2,3,4-trihydroxypentyl, 2,3,4,5-tetrahydroxyhexyl, 3,4,5,6,7-pentahydroxyheptyl, 3,4,5,6-tetrahydroxyheptyl, 2,4,5-trihydroxypentyl, 2,4,5,6-tetrahydroxyhexyl, 2,4,5-trihydroxyhexyl, 2,5-dihydroxypentyl and 2,3-dihydroxypentyl, branched polyhydroxyalkyl radicals, such as 2,4-dihydroxy-3-hydroxymethylpentyl and 2,2-bis-hydroxymethylpropyl, straight-chain polyhydroxyalkyl radicals, such as 4,5-dihydroxy-pent-2-en-1-yl, 4,5,6-trihydroxyhex-2-en-1-yl and 4,5-dihydroxy-hex-2-en-1-yl, and polyhydroxyalkyl groups which are acylated or alkylated on the OH groups such as 2,3,4,5-tetraacetoxypentyl, 2,3,4,5-tetrabenzoyloxyhexyl, 2,3-dimethoxypropyl, 2,3,4-trihydroxy-5-methoxypentyl, 2,3-O-isopropylidenepropyl, 2,3-O-cyclohexylidenepropyl, 1-hydroxymethyl-ethyl, 2-hydroxy-1-hydroxymethyl-ethyl, 3-hydroxy-1-methylpropyl, 3-hydroxy-1-hydroxymethylpropyl, 2,3-dihydroxy-1-hydroxymethyl-propyl, 4-hydroxy-1-methylbutyl, 4-hydroxy-1-hydroxymethyl-butyl, 2,4-dihydroxy-1-hydroxymethyl-butyl, 2,3,4-trihydroxy-1- hydroxymethyl-butyl, 1-hydroxymethyl-propyl, 3-hydroxy-1-(2-hydroxyethyl)-propyl, 1-hydroxymethyl-butyl and 3,4-dihydroxy-1-(1,2-dihydroxyethyl)-butyl.

The radicals listed above are merely illustrative. They all contain at least one, and in most cases several, chiral carbon atom(s) and are in the forms of optically pure diastereomers or diastereomer mixtures. It can be advantageous to use the compounds according to the invention as optically pure products.

Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

Compounds of the present invention in which $R_3$ denotes a hydrogen atom are very particularly preferred.

According to the present invention there is further provided a process for the production of compounds of the invention in which $R_1$ denotes a hydrogen atom comprising reacting a compound of the general formula

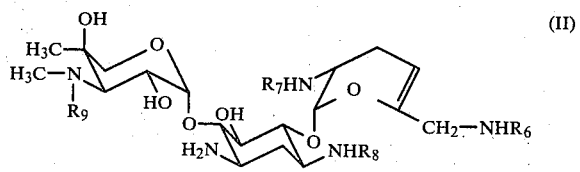

in which $R_6$, $R_7$ and $R_8$ independently denote —CO—$R_{10}$ or —S—$R_{11}$ and $R_9$ denotes —S—$R_{11}$, in which $R_{10}$ denotes a radical of the general formula —CHal$_3$, —(CH$_2$)$_{n_6}$B, —O—E,

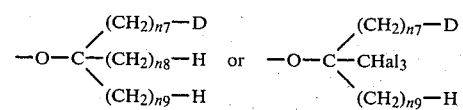

in which

B and D denote a hydrogen atom or an optionally substituted phenyl radical,

E denotes an optionally substituted phenyl radical, $n_6$ is 0, 1, 2, 3, 4 or 5, $n_7$, $n_8$ and $n_9$ are independently 0, 1, 2, 3, 4 or 5, Hal denotes a fluorine, chlorine or bromine atom and $R_{11}$ denotes an optionally substituted phenyl or di- or tri-phenylmethyl radical, with an acylating agent of the general formula

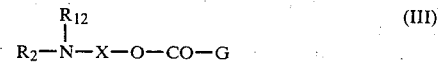

in which $R_2$ and X have the meaning indicated above,

G denotes a leaving group, preferably a halogen atom e.g. a chlorine or bromine atom, an azido radical or an optionally substituted phenoxy radical, or a radical of the formula

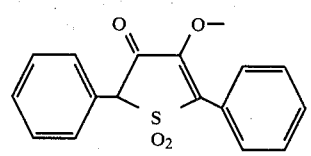

and $R_{12}$ denotes —CO—$R_{10}$ or —S—$R_{11}$ (in which $R_{10}$ and $R_{11}$ have the meaning indicated above), the protective groups $R_6$, $R_7$, $R_8$, $R_9$ and $R_{12}$ and, if appropriate, alkylidene groups which 2 radicals $R_3$ form together, being split off and the resulting compound being converted, if desired, into a salt thereof.

Leaving group G, when optionally substituted phenoxy, is preferably 4-nitrophenoxy, phenoxy and 2,4,5-trichlorophenoxy.

Examples of suitable substituents of the optionally substituted phenyl or di- or tri-phenylmethyl radicals $R_{11}$ are 1 to 3 substituents selected from trifluoromethyl, nitro, $C_1$ to $C_4$ alkyl, $C_1$ to $C_4$ alkoxy, ($C_1$ to $C_4$ alkoxy)-carbonyl and phenyl, or 1 to 5 halogen atoms, preferably chlorine atoms. Examples of —S—$R_{11}$ groups which may be mentioned are o-nitrophenylsulphenyl and 2,4,5-trichlorophenylsulphenyl.

Suitable substituents of the optionally substituted phenyl radicals B, D and E are 1 or 2 substituents selected from nitro, halogen, preferably chlorine, $C_1$ to $C_4$ alkyl, $C_1$ to $C_4$ alkoxy and phenyl.

Examples of suitable acylating agents of formula (III) are

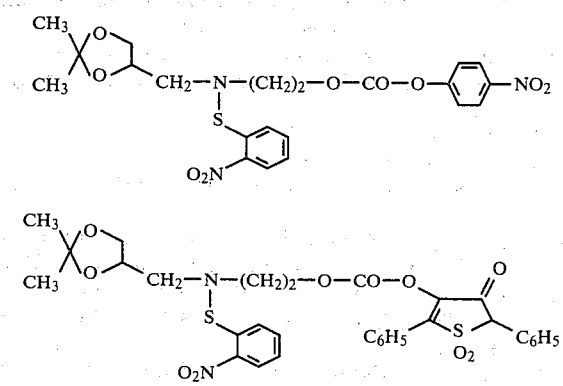

-continued

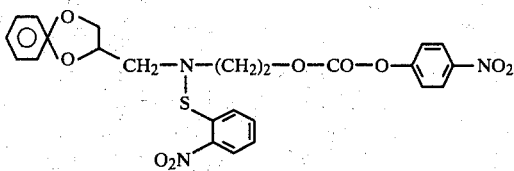
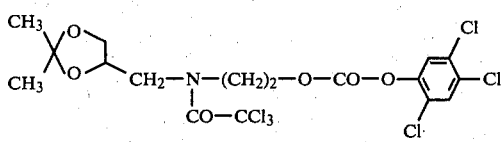
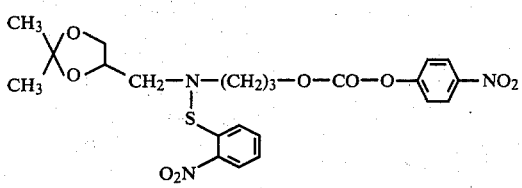
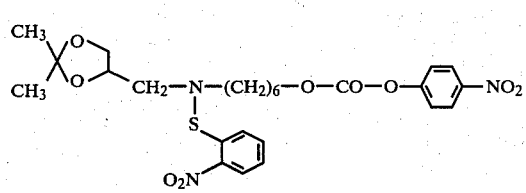
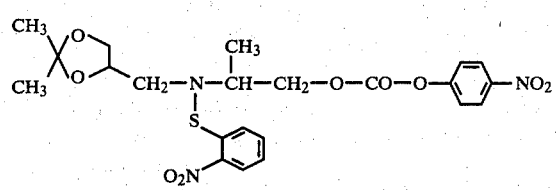
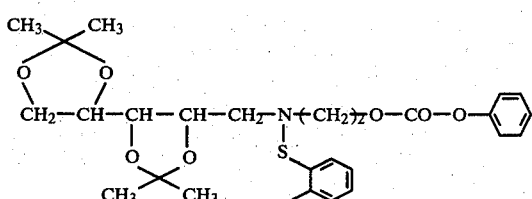

and

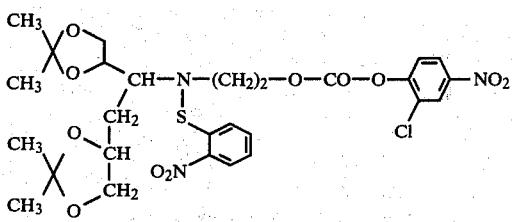

According to the present invention there is further provided a process for the production of compounds of the invention, in which a compound of the general formula

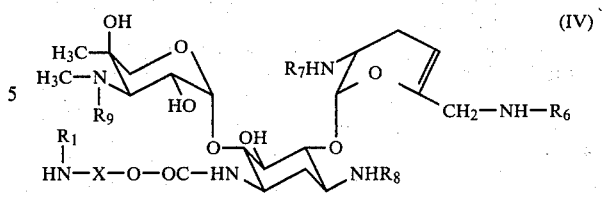 (IV)

in which $R_1$, $R_6$, $R_7$, $R_8$, $R_9$ and X have the meanings indicated above, is reacted with a carbonyl compound of the general formula

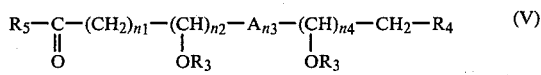 (V)

in which $R_3$, $R_4$, $R_5$, A, $n_1$, $n_2$, $n_3$ and $n_4$ have the meanings indicated above, in the presence of a hydrogen donor reducing agent and the protective groups $R_6$, $R_7$, $R_8$ and $R_9$ and, if approptiate, alkylidene groups which 2 radicals $R_3$ form together, are split off and the resulting product is converted, if desired, into a salt thereof.

The carbonyl compounds of the formula (V) are, for example, glycolaldehyde, e.g. D- or L-glyceraldehyde, aldehyde-sugars, such as D-erythrose, D-ribose, D- or L-arabinose, D-glucose, D-galactose, 2-desoxy-D-ribose, 2-desoxy-D-glucose, 2-desoxy-D-galactose, 6-desoxy-L-mannose, 6-desoxy-D-glucose, 5-desoxy-D-ribose, 2,6-di-desoxy-D-glucose or -L-glucose, 3-O-methyl-D-glucose and 5-O-methyl-D-ribose, and ketones, such as, for example, hydroxyacetone, methoxyacetone, dihydroxyacetone, 4-hydroxy-2-butanone, 1,4-dihydroxy-2-butanone, 1,3,4-trihydroxy-2-butanone, 5-hydroxy-2-pentanone, 1,5-dihydroxy-2-pentanone, 1,3,5-trihydroxy-2-pentanone, 1,3,4,5-tetrahydroxy-2-pentanone, 1-hydroxy-2-butanone, 1,5-dihydroxy-3-pentanone, 1-hydroxy-2-pentanone and 1,2,5,6-tetrahydroxy-3-hexanone. Furthermore, carbonyl compounds, the hydroxyl groups of which are blocked by suitable protective groups can also be used. Examples which may be mentioned are: 2,3-O-isopropylidene-D-glyceraldehyde, 2,3-O-cyclohexylidene-D-glyceraldehyde, 4,5-O-cyclohexylidene-2,3-didesoxy-D,L-ribose and 4-(tetrahydropyran-2-yloxy)-2-buten-1-al.

Starting substances of the formula (II) which are preferably used are 2',3,3'',6'-tetra-N-(o-nitrophenylsulphenyl)-sisomicin, 3''-N-(o-nitrophenylsulphenyl)-2',3,6'-tris-N-trichloroacetyl-sisomicin, 3''-N-(o-nitrophenylsulphenyl)-2',3,6'-tris-N-trifluoroacetyl-sisomicin, 3''-N-(o-nitrophenylsulphenyl)-2',3,6'-tris-N-(2,2,2-trichloroethoxycarbonyl)-sisomicin, 3''-N-(o-nitrophenylsulphenyl)-2',3,6'-tris-N-(1,1-dimethyl-2,2,2-trichloroethoxycarbonyl)-sisomicin, 3''-N-(o-nitrophenylsulphenyl)-2',3,6'-tris-N-(4-methoxybenzyloxycarbonyl)-sisomicin, 3''-N-(o-nitrophenylsulphenyl)-2',3,6'-tris-N-phenoxycarbonylsisomicin and 3''-N-(o-nitrophenylsulphenyl)-2',3,6'-tris-N-(tert.-butoxycarbonyl)-sisomicin, and these compounds are prepared by the process described in DE-OS (German Published Specification) 2,726,197, or via the following stages:

(1) Reaction of penta-N-(o-nitrophenylsulphenyl)-sisomicin (German Offenlegungsschrift (German Published Specification) 2,726,197) with dimethyl-(1,2-dimethylpropyl)-silyl chloride to give penta-N-

(o-nitrophenylsulphenyl)-2''-O-[dimethyl-(1,2-dimethylpropyl)-silyl]-sisomicin;
(2) Splitting off of the o-nitrophenylsulphenyl groups of the 2'-, 3- and 6'-N with 2-mercaptobenzthiazole;
(3) Acylation of the 2'-, 3- and 6'-N positions with a customary acylating agent;
(4) Splitting off of the 2''-O-protective group and
(5) Splitting off of the 1-N-(o-nitrophenylsulphenyl) group.

The compounds of the formula (IV) used as an intermediate product are obtained when a compound of the formula (II) is reacted with an acylating agent of the formula

in which
R$_1$, R$_{12}$, X and G have the meanings indicated above, to give a compound of the formula

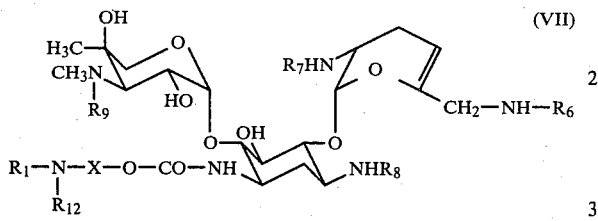

in which
R$_1$, R$_6$, R$_7$, R$_8$, R$_9$, R$_{12}$, and X have the above-mentioned meanings,
and the protective group R$_{12}$ is then split off selectively in the presence of the protective groups R$_6$, R$_7$, R$_8$ and R$_9$.

The compounds of the formula (VI) used as acylating agents can be prepared by conventional processes by linking an aminoalcohol to the protective group R$_{12}$ at the amino group and converting the alcohol group into a reactive carbonate. Examples which may be mentioned are: 4-nitrophenyl 2-trifluoroacetylaminoethyl carbonate, 2,4,5-trichlorophenyl 3-trifluoroacetylaminopropyl-1-yl carbonate, 4-nitrophenyl 2-(2-nitrophenylsulphenylamino)-ethyl carbonate, 4-nitrophenyl 6-trifluoroacetylaminohex-1-yl carbonate, 4-nitrophenyl 2-trichloroacetylaminoethyl carbonate, 2,4,5-trichlorophenyl 4-trichloroacetylbut-1-yl carbonate, 4-nitrophenyl 2-trichloroacetylaminoprop-1-yl carbonate, 4-nitrophenyl 2-trifluoroacetyl-methylaminoethyl carbonate, 4-nitrophenyl 2-trichloroacetyl-benzylamino-ethyl carbonate and chloroformic acid 2-trichloroacetylaminoethyl ester.

In carrying out the process according to the invention by the method first mentioned, 1 mol of the compound of the formula (II) is preferably reacted with 1 to 3 mols, more preferably 1.1 to 1.5 mols, of a compound of the formula (III), possible diluents being all the inert organic solvents, such as toluene, chloroform, methylene chloride, dimethylformamide, dimethylacetamide, dimethylsulphoxide, ethers, such as diethyl ether, dioxane and tetrahydrofurane, pyridine, alcohols, such as methanol and ethanol, and mixtures thereof.

If acid-binding agents are required, any of the customary organic and inorganic acid-binding agents can be used. These include, preferably, alkali metal hydroxides and alkaline earth metal hydroxides, such as sodium hydroxide, potassium hydroxide or calcium hydroxide, alkali metal carbonates and bicarbonates and alkaline earth metal carbonates and bicarbonates, such as sodium carbonate, potassium carbonate, sodium bicarbonate and calcium carbonate, calcium oxide, tertiary aliphatic and aromatic amines, such as triethylamine and N,N-dimethylaniline, and heterocyclic bases, such as pyridine and quinoline.

The reaction temperatures can be varied within a wide range. Preferably, the reaction is carried out at temperatures from $-30°$ C. to $+80°$ C., more preferably between $0°$ C. and $+40°$ C.

The reaction can be carried out under normal pressure, but also under increased pressure. Preferably, it is carried out under normal pressure.

For carrying out the process according to the invention by the second method, 1 mol of a compound of the formula (IV) is preferably reacted with 1 to 3 mols, more preferably 1.1 to 1.5 mols, of a compound of the formula (V) preferably in the presence of 1 to 3 mols, more preferably 1.1 to 1.5 mols, of a hydrogen donor reducing agent.

Hydrogen donor reducing agents which are used in this process include dialkylamino boranes, for example dimethylaminoborane, diethylaminoborane and morpholinoborane, tetraalkylammonium cyanoborohydrides, for example tetrabutylammonium cyanoborohydride, alkali metal borohydrides, for example sodium borohydrides, and, preferably, alkali metal cyanoborohydrides, for example lithium cyanoborohydride and sodium cyanoborohydride.

The process is preferably carried out in an inert solvent. The solvent can be an organic or inorganic solvent in which the selectively protected compound of the formula (IV) and the other reagents are soluble and which as far as possible suppresses or prevents side reactions under the reaction conditions. Although anhydrous aprotic solvents, for example tetrahydrofurane, can advantageously be employed, if the reducing agent is morpholinoborane, a protic solvent is nevertheless usually used. Examples of suitable protic solvents are a $C_1$–$C_6$ alkanol or, preferably, water or an aqueous $C_1$–$C_6$ alkanol, preferably aqueous methanol or ethanol, or other solvent systems which contain water, such as aqueous dimethylformamide, aqueous hexamethylphosphoramide, aqueous tetrahydrofurane or aqueous ethylene glycol dimethyl ether.

The process is preferably carried out in a pH range from 1 to 11, and more preferably at pH 4 to 8.

Reductive alkylation with a carbonyl compound of the formula (V) in the presence of a hydrogen donor reducing agent is usually carried out at room temperature in the presence of air, although it can be more favourable to carry out the reaction under an inert gas (e.g. argon or nitrogen). The reaction usually goes to completion very rapidly, frequently in less than 60 minutes, which can be established by determinations by thin layer chromatography.

When the reaction of the compounds of formula (II) and (III) or (IV) and (V) has ended, the protective groups contained in the molecule are removed.

The sulphenyl protective groups can be split off with weak acids or with sulphur-containing, nucleophilic reagents, such as, for example, H$_2$S, thiophenol or 2-mercaptobenzthioazole, and the remaining protective groups can be split off with aqueous alkali metal hydroxide or alkaline earth metal hydroxide or with acids, such as trifluoroacetic acid, perchloric acid or boron trifluorideetherate.

If 3''-N-(o-nitrophenylsulphenyl)-3,2',6'-tris-N-(trichloroacetyl)-sisomicin and 2-[N-(2,3-O-cyclohexylidenedioxypropyl)-N-(o-nitrophenylsulphenyl)amino]-ethyl 4-nitrophenyl carbonate are used as starting substances, the course of the reaction can be represented by the following equation, as an example of the method first mentioned.

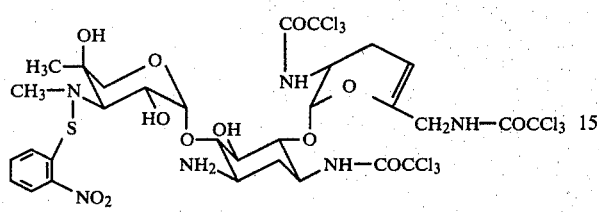

If 1-N-(2-aminoethoxycarbonyl)-3,2',6',3''-tetra-N-(o-nitrophenylsulphenyl)-sisomicin and dihydroxyacetone are used as starting substances, the course of the reaction can be represented by the following equation, as an example of the second method:

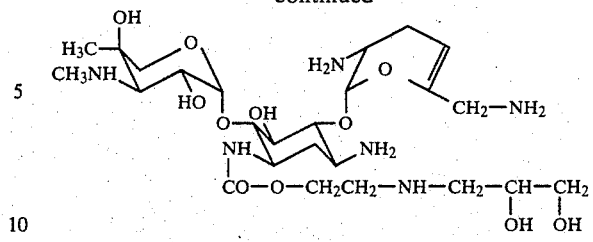

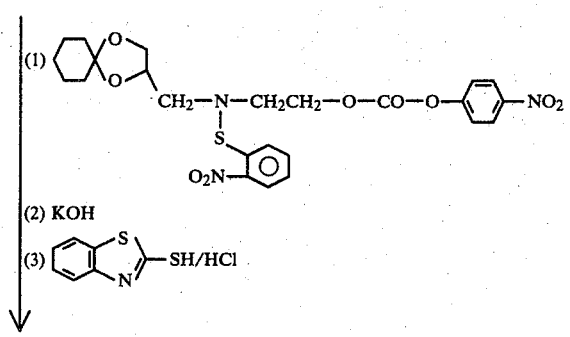

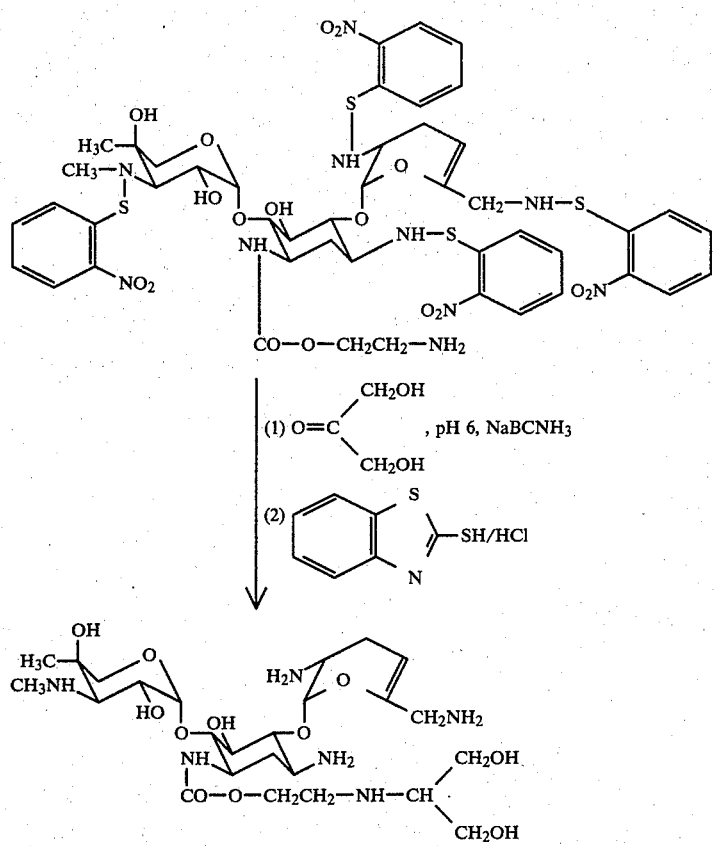

The compounds according to the invention are antimicrobial agents with a broad action spectrum and a particular activity against Gram-negative bacteria. These properties enable them to be used as medicaments, especially in combating illnesses, in warm-blooded animals, caused by bacteria. They are suitable for the prophylaxis and chemotherapy, in medicine, of local and systemic infections, especially infections of the urogenital system, which are caused by Gram-negative bacteria, for example E. coli, Proteus, Klebsiella and Pseudomonas. Inhibition areolae in the agar hole test were found, for example, against the following strains of bacteria, at a concentration of 100 micrograms/1 ml: Pseudomonas aerug. 5737, Pseudomonas aerug. F 41, Klebsiella pneum. 2 Munich, Klebsiella pneum.; Düsseldorf, E. coli Münster and E. coli Neumann.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose, or for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

Topical pharmaceutical compositions according to the invention generally contain from 0.1 to 3.0 g of the active ingredient per 100 g of ointment, cream or lotion.

In addition, to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent. The dosage of the compounds according to the invention is usually similar to the dosage of the 1-N-substituted compounds. The dosage range is from 20 mg/day/subject to 2000 mg/day/subject, and is preferably 100 mg–500 mg/day.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or topically, preferably orally, topically or parenterally. Preferred pharmaceutical compositions and medicaments are therefore those adapted for administration such as oral, topical or parenteral administration. Administration in the method of the invention is preferably oral, topical or parenteral administration.

In general it has proved advantageous to administer amounts of from 1 mg to 15 mg/kg of body weight per day in 2 to 4 doses daily, in the case of parenteral or oral administration, to achieve effective results. Topical application is effected preferably 2 to 5 times per day in concentrations of 0.1 g to 3.0 g of active ingredient per 100 g of ointment, paste, lotion, cream or gel. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day. In the case of oral veterinary administration, the compound can also be admixed to the animal feed and to the drinking water.

The following are Examples of particularly preferred formulations according to the present invention.

| Formulation 1 Tablet | 10mg tablet | | 25mg tablet | | 100mg tablet | |
| --- | --- | --- | --- | --- | --- | --- |
| Compound according to Example 31 | 10.50+ | mg | 26.25+ | mg | 105.00+ | mg |
| Lactose | 197.50 | mg | 171.25 | mg | 126.00 | mg |
| Maize starch | 25.00 | mg | 25.00 | mg | 35.00 | mg |
| Polyvinyl-pyrrolidone | 7.50 | mg | 7.50 | mg | 7.50 | mg |
| Magnesium stearate | 2.50 | mg | 2.50 | mg | 3.50 | mg |

+5% excess

To prepare the tablets, a suspension of the compound according to Example 31, lactose and polyvinylpyrrolidone is prepared and this is spray-dried. The maize starch and magnesium stearate are added and the mixture is pressed to tablets.

| Formulation 2 Ointment | |
| --- | --- |
| Compound according to Example 31 | 1.0 g |
| Methylparaben U.S.P. | 0.5 g |
| Propylparaben U.S.P. | 0.1 g |
| Petrolatum | to 1,000 g |

Preparation (1) The petrolatum is melted;
(2) the compound according to Example 31, Methylparaben and Propylparaben are mixed with about 10% of the molten Petrolatum;
(3) the mixture is introduced into a colloid mill;
(4) the remaining petrolatum is added, whilst stirring, and the mixture is cooled until it becomes semi-solid. The product is filled into suitable containers.

| Formulation 3 Injection solution | Per 2.0 ml phial | per 50 liters |
| --- | --- | --- |
| Compound according to Example 31 | 84.0 mg+ | 2,100.0 gm |
| Methylparaben U.S.P. | 3.6 mg | 90.0 gm |
| Propylparaben U.S.P. | 0.4 mg | 10.0 gm |
| Sodium bisulphate, U.S.P. | 6.4 mg | 160.0 gm |
| Disodium ethylene-diaminetetraacetate dihydrate | 0.2 mg | 5.0 mg |
| Water U.S.P., q.s. | 2.0 mg | 50.0 liters |

+5% excess

The following Examples illustrate processes for the production of compounds according to the present invention.

EXAMPLE 1

Penta-N-(o-nitrophenylsulphenyl)-2"-O-[dimethyl-(1,2-dimethylpropyl)-silyl]-sisomicin 60.6 g of crude penta-N-(o-nitrophenylsulphenyl)-sisomicin (DE-OS (German Published Specification) No. 2,726,197) and 8.75 g of imidazole are dissolved in 250 ml of absolute methylene chloride. 22.5 ml of dimethyl-(1,2-dimethyl-propyl)-silyl chloride are added dropwise at 0° C., with exclusion of moisture. The batch is evaporated in vacuo to about 170 ml and left to stand at room temperature for 48 hours. After adding 130 ml of absolute methylene chloride, the precipitate is filtered off, that the filtrate is thoroughly shaken vigorously with 350 ml of petroleum ether and the petroleum ether phase is decanted off and discarded. The oil which has separated out is dissolved in 100 ml of methylene chloride and the product is separated out again with 250 ml of petroleum ether and finally dried under a high vacuum. Yield: 60 g (89%) of crude product, which can be employed for subsequent reactions without further purification. A pure product is obtained by chromatography on silica gel using $CH_2Cl_2/CH_3OH=99/1$.

$^{13}C$-NMR ($CDCl_3$): $\delta = 124-138$ (aromatic C); 147.54 (C-5'); 102.26 (C-1"); 97.81 (C-4'); 99.09 (C-1'); −2.9 to −3.0 (Si-$CH_3$); 22.77

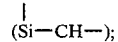

and 30.60

ppm.

Penta-N-(o-nitrophenylsulphenyl)-2″,5-bis-O-[dimethyl-(1,2-dimethyl-propyl)-silyl]-sisomicin is isolated as a by-product.

$^{13}$C-NMR (CDCl$_3$): δ=124–146 (aromatic C); 148.00 (C-5′); and 96.13 ;1 (C-4′) ppm.

EXAMPLE 2

1,3″-Bis-N-(o-nitrophenylsulphenyl)-2″-O-[dimethyl-(1,2-dimethyl-propyl)-silyl]-sisomicin 16 g of 2-mercapto-benzthiazole are added to 56 g of crude penta-N-(o-nitrophenylsulphenyl)-2″-O-[dimethyl-(1,2-dimethyl-propyl)-silyl]-sisomicin in 36 ml of methylene chloride/70 ml of methanol, the mixture is shaken until a clear solution is obtained and the solution is left to stand at 5° C. for 2 hours. The precipitate which thereby separates out is filtered off and the solution is used for the subsequent reactions without isolation of the desired product. The yield is about 80% of theory. To prepare a pure product, the filtrate is evaporated rapidly in vacuo and the residue is chromatographed on silica gel using (a) methylene chloride, (b) methylene chloride/CH$_3$OH (8:2) and (c) CH$_2$Cl$_2$/CH$_3$OH/20% strength aqueous ammonia (7:2.7:0.3). The yield of pure product is 25.3 g (69%).

$^{13}$C-NMR (CD$_3$OD): δ=1.5 (Si-CH$_3$); 122–146 (aromatic C); 147.14 (C-5′); 103.31 (C-1″); 100.16 (C-1′); and 99.30 (C-4′) ppm 3 g (10%) of 3″-N-(o-nitrophenylsulphenyl)-2″-O-[dimethyl-(1,2-dimethyl-propyl)-silyl]-sisomicin are isolated as a by-product during the column chromatography.

$^{13}$C-NMR (CD$_3$OD): δ=76.66 (C-2″); 21.70 (C-6″); 30.40 (N-CH$_3$); 53.13 (C-1), 52.18 (C-3); 44.06 (C-6′); and 49.41 (C-2′) ppm

EXAMPLE 3

1,3″-Bis-N-(o-nitrophenylsulphenyl)-2′,3,6′-tris-N-tri-chloroacetyl-2″-O-[dimethyl-(1,2-dimethyl-propyl)-silyl]-sisomicin 7.5 ml of trichloroacetic anhydride are added dropwise to 8.8 g of 1,3″-bis-N-(o-nitrophenylsulphenyl)-2″-O-[dimethyl-(1,2-dimethyl-propyl)-silyl]-sisomicin in 20 ml of methylene chloride/20 ml of pyridine at −15° C. and the mixture is further stirred, at room temperature, for another 10 minutes. After adding 20 ml of methylene chloride, the batch is extracted by shaking twice with 20 ml of H$_2$O each time, the organic phase is evaporated and the residue is further processed as the crude product. R$_F$ (CH$_2$Cl$_2$/CH$_3$OH=97.5/2.5)=0.72.

EXAMPLE 4

1,3″-Bis-N-(o-nitrophenylsulphenyl)-2′,3,6′-tris-N-trichloroacetyl-sisomicin

The crude oil from Example 3 is dissolved in 20 ml of dimethylsulphoxide, 2 ml of a 50 percent strength KF solution are added and the mixture is stirred vigorously for 3 hours. The product is precipitated with water, washed with water and dried. The crude product is subsequently processed without further purification.

$^{13}$C-NMR (CDCl$_3$): δ=103.60 (C-1″); 66.48 (C-3″); 55.15 (C-1); 50.60 (C-3); 79.86 (C-4); 76.18 (C-5); 89.16 (C-6); 97.74 (C-1′); 96.84 (C-4′); 149.80 (C-5′); 92.78 (CCl$_3$); and 162.29 and 162.11 (CO) ppm.

EXAMPLE 5

3″-N-(o-Nitrophenylsulphenyl)-2′,3,6′-tris-N-trichloroacetyl-sisomicin

The product from Example 4 is dissolved in 13 ml of methylene chloride, the solution is shaken with 26 ml of methanol and 5 g of 2-mercaptobenzthiazole until a clear solution is obtained and this solution is left to stand at 5° C. for 3 days. The precipitate is filtered off, the filtrate is evaporated and the residue is chromatographed on silica gel (running agent a: CH$_2$Cl$_2$/CH$_3$OH=95/5; b: (CH$_2$Cl$_2$/CH$_3$OH/20% strength aqueous NH$_3$=93/6.5/0.5).

$^{13}$C-NMR (CDCl$_3$): δ=103.43 (C-1″); 67.46 (C-3″); 50.85 (C-1); 50.28 (C-3); 79.44 (C-4); 76.51 (C-5); 89.29 (C-6); 97.61 (C-1′); 96.62 (C-4′); 149.50 (C-5′); 92.46 and 92.38 (CCl$_3$); and 162.01 and 161.76 (CO) ppm.

EXAMPLE 6

4-Nitrophenyl 2-trifluoroacetylaminoethyl carbonate 52.5 g of trifluoroacetic anhydride are added to 30.5 g of 2-aminoethanol in 200 ml of acetonitrile, whilst cooling with ice, the temperature being kept between 5° and 20° C. When the reaction has subsided, the mixture is concentrated and the residue is fractionated. Yield: 37.5 g of 2-(trifluoroacetylamino)-ethanol of boiling point 130°–131° C./11 mm (slowly crystallises completely).

17 g (0.108 mol) of 2-(trifluoroacetylamino)-ethanol are dissolved in 210 ml of pyridine, 21 g of chloroformic acid 4-nitrophenyl ester are added and the mixture is left to stand overnight at room temperature. It is then concentrated, the residue is taken up in methylene chloride and the methylene chloride mixture is washed with ice-water and dried with Na$_2$SO$_4$. After evaporating off the solvent, 33 g of a light-coloured oil are obtained.

IR: 1720 and 1770/cm. The product contains about 30% of 4-nitrophenol.

EXAMPLE 7

4-Nitrophenyl 3-trifluoroacetylaminopropyl carbonate

The activated carbonate, IR: 1710 and 1765/cm, is prepared analogously to Example 6 from 3-(trifluoroacetylamino)-propan-1-ol (boiling point 120° C./3 mm; IR: 1710/cm).

EXAMPLE 8

4-Nitrophenyl 6-trifluoroacetylaminohex-1-yl carbonate

The activated carbonate is obtained as the crude product, IR: 1720 and 1770/cm, analogously to Example 6 from 6-(trifluoroacetylamino)-hexan-1-ol (boiling point 150°–154° C./3.5 mm; IR: 1710/cm).

EXAMPLE 9

4-Nitrophenyl 2-(2-nitrophenylsulphenyl-methyl-amino)-ethyl carbonate

A solution of 1.4 g of 2-methylamino-ethanol in 30 ml of dioxane is initially introduced into the reaction vessel and a solution of 3.8 g of o-nitrophenylsulphenic acid chloride in 10 ml of dioxane, and 8.5 ml of 2 N sodium hydroxide solution are simultaneously added dropwise, whilst maintaining a pH of 8. After stirring the mixture at room temperature for several hours, it is concentrated in vacuo, the residue is taken up in ethyl acetate and the ethyl acetate mixture is washed twice with water, dried with $Na_2SO_4$ and concentrated in vacuo. The oil which remains is chromatographed over 100 g of silica gel using toluene/ethyl acetate (2:1) and the main component ($R_f$: 0.29) is separated off. Yield: 2.9 g of N-(2-hydroxyethyl)-N-methyl-o-nitrosulphenic acid amide; melting point: 53°–56° C.

456 mg of this compound and 600 mg of chloroformic acid p-nitrophenyl ester are dissolved in 5 ml of acetonitrile, and 300 mg of triethylamine in 5 ml of acetonitrile are added, whilst cooling with ice. After 1 hour at room temperature, the mixture is concentrated in vacuo, the residue is taken up in 30 ml of methylene chloride, the methylene chloride mixture is washed twice with water, dried with $Na_2SO_4$ and concentrated in vacuo, the resulting orange oil is chromatographed over 100 g of silica gel using toluene/ethyl acetate (2:1) and the main fraction is separated off. Yield: 250 ml of an orange oil which slowly crystallises completely.

IR (KBr): 1770 cm$^{-1}$. $R_f$ value (toluene/ethyl acetate 2:1): 0.84.

EXAMPLE 10

4-Nitrophenyl 2-(2-nitrophenylsulphenylamino)-ethyl carbonate

The procedure followed is analogous to Example 9; IR: 1770 cm$^{-1}$; $R_f$ value (toluene/ethyl acetate 2:1):0.77.

EXAMPLE 11

1-N-(2-Aminoethoxycarbonyl)-3,2′,6′,3″-tetra-N-(o-nitrophenylsulphenyl)-sisomicin 3.3 g of 3,2′,6′,3″-tetra-N-(o-nitrophenylsulphenyl)-sisomicin (DE-OS (German Published Specification) No. 2,726,197) are dissolved in 15 ml of pyridine, 3.5 g of the product from Example 6 are added, the mixture is stirred at room temperature and the course of the reaction is followed by thin layer chromatography (precoated silica gel plates; running agent: methylene chloride/methanol=95/5). After leaving to stand overnight, the mixture is concentrated under a high vacuum, the residue is taken up in 140 ml of methylene chloride/60 ml of methanol, and 6 ml of 4 N NaOH are added dropwise, whilst stirring. After 1 hour at room temperature, splitting off of the protective groups has ended. The NaOH phase is separated off and the organic phase is washed with water until it no longer gives a basic reaction. After drying with $Na_2SO_4$, the organic phase is evaporated in vacuo and the residue is chromatographed on 200 g of silica gel in order to separate off some non-polar impurities, the column being eluted first with methylene chloride and then with methylene chloride/methanol (5:1).

Yield: 2.2 g of an orange solid product; $R_f$ value (methylene chloride/methanol 5:1): 0.4

EXAMPLE 12

1-N-(3-Aminopropoxycarbonyl)-3,2′,6′,3″-tetra-N-(o-nitrophenylsulphenyl)-sisomicin The procedure followed is as according to Example 11, using the activated carbonate from Example 7, and the reaction product is obtained in 55% yield. $R_f$ value (methylene chloride/methanol 5:1): 0.42.

EXAMPLE 13

1-N-(6-Aminohexyloxycarbonyl)-3,2′,6′,3″-tetra-N-(o-nitrophenylsulphenyl)-sisomicin The procedure followed is as according to Example 11, using the carbonate from Example 8, and the sisomicin derivative is obtained in 52% yield. $R_f$ value (methylene chloride/methanol 5:1): 0.5.

EXAMPLE 14

1-N-(2-Aminoethoxycarbonyl)-3″-N-(o-nitrophenylsulphenyl)-3,2′,6′-tris-N-(trichloroacetyl)-sisomicin 500 mg of the product from Example 10 are added to a solution of 1.04 g of the product from Example 5 in 5 ml of pyridine and the mixture is stirred at room temperature. After 2 hours, no further starting compound can be detected by thin layer chromatography (precoated silica gel plates, running agent=methylene chloride/methanol/20% aqueous $NH_3$=930/65/5). The mixture is evaporated under a high vacuum, the residue is taken up in methylene chloride and the methylene chloride mixture is washed with water, dried with $Na_2SO_4$ and concentrated again. To split off the NPS group from the primary amino group, the residue is taken up in 3 ml of methanol/2 ml of methylene chloride, 170 mg of 2-mercaptobenzthiazole are added and the mixture is left to stand at room temperature for 1 day. Thereafter, it is concentrated and the polar product obtained by splitting off the protective groups is purified by chromatography on 70 g of silica gel (running agent as above) to remove some non-polar components. Yield: 577 mg of an orange solid product. $R_f$ value (running agent as above): 0.15.

EXAMPLE 15

1-N-(2-Methylaminoethoxycarbonyl)-3″-N-(o-nitrophenylsulphenyl)-3,2′,6′-tris-N-(trichloroacetyl)-sisomicin The procedure followed is analogous to Example 14, and the sisomicin derivative is obtained in 45% yield. $R_f$ value (methylene chloride/methanol/20% strength $NH_3$=930/65/5): 0.17.

EXAMPLE 16

1-N-[2-(1,3-Dihydroxypropyl-2-amino)-ethoxycarbonyl]-sisomicin 115 mg of the product from Example 11 are dissolved in 2.5 ml of methanol/0.4 ml of methylene chloride/0.5 ml of water, the pH is adjusted to 6 with acetic acid and 20 mg of dihydroxyacetone are added. The mixture is stirred at room temperature for 15 minutes and 15 mg of $NaBCNH_3$ are then added. After another 30 minutes, a new product can be detected by thin layer chromatography (thin layer chromatogram: silica gel; methylene chloride/methanol=5:1; $R_f$ value=0.53), and is isolated by adding 5 ml of ethyl acetate, washing the mixture with 2×5 ml of water and drying it with Na$_2$SO$_4$ and concentrating the filtrate in vacuo. The o-nitrophenylsulphenyl protective groups are split off by dissolving the residue in 0.6 ml of methylene chloride, adding 1.6 ml of a solution of 8.5 g of 2-mercaptobenzthiazole in 30 ml of methanol/50 ml of methylene chloride and acidifying the mixture with dilute hydrochloric acid until it becomes light in colour. The sisomicin derivative is extracted, with 1 ml of water, from the solution obtained from splitting off the protective groups and the aqueous phase is washed with 2×0.5 ml of methylene chloride and rendered basic with the basic ion exchanger Lewatit MP 500 (OH$^-$). The mixture is evaporated and the residue is chromatographed over 5 g of silica gel using methylene chloride/methanol/20% strength NH$_3$ (2:4:1) as the running agent, to remove a few impurities; yield=29 mg. R$_f$ value (silica gel, methylene chloride/methanol/concentrated NH$_3$=2:2:1): 0.44.

The R$_f$ values given in the following embodiment examples were determined on thin layer chromatography plates pre-coated with silica gel 60 F$_{254}$ from Messrs. Merck, Darmstadt. Unless otherwise indicated, the running agent system methylene chloride/methanol/20% strength aqueous NH$_3$ solution (2:4:1) was used. For staining of the substances, the plates were exposed to iodine vapour in a chamber.

Silica gel 60 (0.063–0.2 mm) from Messrs. Merck, Darmstadt, was used for the purification by chromatography.

EXAMPLE 17

1-N-{2-[(S)-2,3-Dihydroxypropylamino]-ethoxycarbonyl}-sisomicin

The procedure followed is as in Example 16, but 2,3-O-isopropylidene-D-glyceraldehyde is used as the carbonyl component and the mixture is heated under reflux for 2½ hours. After splitting off the o-nitrophenylsulphenyl protective groups, the acid reaction solution is left to stand overnight to remove the isopropylidene protective group. Subsequent purification by chromatography on silica gel using methylene chloride/methanol/20% strength NH$_3$ (2:4:1) as the eluting agent gives 17 mg of product with an R$_f$ value of 0.31; the product is identical to the product from Example 31 f.

EXAMPLE 18

1-N-[2-(1-Hydroxypropyl-2-amino)-ethoxycarbonyl]-sisomicin

The procedure followed is as in Example 16, but hydroxyacetone is used as the carbonyl reagent. Yield: 22 mg; R$_f$ value: 0.28

EXAMPLE 19

1-N-{2-[(S,R)-2,3,4-Trihydroxybutylamino]-ethoxycarbonyl}-sisomicin

The procedure followed is as in Example 16, but D-erythrose is used as the carbonyl reagent. Yield: 15 mg; R$_f$ value: 0.28.

EXAMPLE 20

1-N-[2-(4-Hydroxy-but-2-enylamino)-ethoxycarbonyl]-sisomicin

The procedure followed is as in Example 16, but 4-(2-tetrahydropyranyl)-but-2-en-1-al (E. J. Corey and J. W. Suggs Tetrahedron Letters 1975, 2647) is used as the carbonyl reagent. After splitting off the o-nitrophenylsulphenyl protective groups with 2-mercaptobenzthiazole/HCl, the acid solution is left to stand, at room temperature, for another 2 hours in order to additionally remove the tetrahydropyranyl protective group. Only then is the solution treated with the anionic exchanger Lewatit MP 500 (OH$^-$), and the reaction product purified. Yield: 12 mg; R$_f$ value: 0.40.

EXAMPLE 21

1-N-[2-(4-Hydroxybut-2-ylamino)-ethoxycarbonyl]-sisomicin

The procedure followed is as in Example 16, but 4-hydroxybutan-2-one is used as the carbonyl component. Yield: 12 mg; R$_f$ value: 0.44

EXAMPLE 22

1-N-{2-[(S,S,R)-2,3,4,5-Tetrahydroxypentylamino]-ethoxycarbonyl}-sisomicin

The procedure followed is as in Example 16, but D-ribose is used as the carbonyl component and the mixture is heated under reflux for 30 minutes. Yield: 13 mg; R$_f$ value: 0.28.

EXAMPLE 23

1-N-{2-[(R,S,R)-2,3,4,5-Tetrahydroxypentylamino]-ethoxycarbonyl}-sisomicin

The procedure followed is as in Example 16, but D-arabinose is used and the mixture is heated under reflux for 30 minutes. Yield: 20 mg; R$_f$ value: 0.46 (methylene chloride/methanol/concentrated NH$_3$=2:2:1) (Sisomicin: 0.51).

EXAMPLE 24

1-N-{2-[(S,R,S)-2,3,4,5-Tetrahydroxypentylamino]-ethoxycarbonyl}-sisomicin 115 mg of the product from Example 11 are dissolved in (a) 2.5 ml of tetrahydrofurane/0.5 ml of water, (b) 2.5 ml of ethanol/0.5 ml of water, (c) 2.5 ml of isopropanol/0.5 ml of water or (d) 2.5 ml of tert.-butanol/0.5 ml of water, the slution is adjusted to pH 6 with acetic acid, 20 mg of L-arabinose are added and the mixture is stirred at room temperature for 30 minutes. Thereafter, 15 mg of NaBCNH$_3$ are added, the mixture is stirred at room temperature for 4 hours and concentrated and the residue is treated with methylene chloride/water. The methylene chloride phase is dried with Na$_2$SO$_4$ and concentrated and the residue is chromatographed on silica gel using methylene chloride/methanol (5:1) as the running agent, to isolate the orange main component. Further working up is carried out as in Example 16 and the following yields are obtained: (a) 9 mg, (b) 11 mg, (c) 14 mg or (d) 13 mg. R$_f$ value: 0.44 (methylene chloride/methanol/concentrated NH$_3$=2:2:1).

EXAMPLE 25

1-N-[2-(4,5-Dihydroxy-pentylamino)-ethoxycarbonyl]-sisomicin (a) 4,5-Cyclohexylidenedioxy-pentan-1-ol:

12 g of 1,2,5-trihydroxypentane are heated with 9.8 g of cyclohexanone and 250 mg of p-toluenesulphonic acid in 50 ml of toluene for 7 hours using a water separator. The mixture is then washed with 5% strength K$_2$CO$_3$ solution and water, dried with Na$_2$SO$_4$ and distilled. Yield: 9 g of boiling point 128°/8 mm.

(b) 4,5-Cyclohexylidenedioxy-pentan-1-al: oxidation of 4,5-cyclohexylidenedioxy-pentan-1-ol with pyridinium chlorochromate in accordance with the method of E. J. Corey et al, Tetrahedron Letters 1975, 2647 gives the aldehyde.

(c) 1-N-[2-(4,5-Dihydroxy-pentylamino)-ethoxycarbonyl]-sisomicin:

The procedure followed is as in Example 16, using 4,5-cyclohexylidenedioxy-pentan-1-al as the carbonyl reagent. After splitting off the o-nitrophenylsulphenyl groups, the cyclohexylidene protective groups are split off by leaving the acid solution to stand. Yield: 13 mg; $R_f$ value: 0.45.

EXAMPLE 26

1-N-{2[(S,R,R,R)-2,3,4,5,6-Pentahydroxy-hexylamino]-ethoxycarbonyl}-sisomicin

The procedure followed is as in Example 16, using D-glucose as the carbonyl reagent and extending the reaction time to 16 hours. $R_f$ value: 0.35 (methylene chloride/methanol/concentrated $NH_3 = 2:2:1$).

EXAMPLE 27

1-N-{3-[(S)-2,3-Dihydroxypropylamino]-propoxycarbonyl}-sisomicin

The procedure followed is as in Example 17, using the intermediate product from Example 12. Yield: 15 mg; $R_f$ value: 0.32.

EXAMPLE 28

1-N-{6-[(S)-2,3-Dihydroxypropylamino]-hexyloxycarbonyl}-sisomicin

The procedure followed is as in Example 17, using the intermediate produce from Example 13. Yield: 12 mg; $R_f$ value: 0.40

EXAMPLE 29

1-N-[3-(1,3-Dihydroxyprop-2-ylamino)-propoxycarbonyl]-sisomicin

The procedure followed is as in Example 16, using the intermediate product from Example 12. Yield: 10 mg; $R_f$ value: 0.46.

EXAMPLE 30

1-N-{2-[(S)-2,3-Dihydroxypropylamino]-ethoxycarbonyl}-sisomicin

The procedure followed is as in Example 17, using the intermediate product from Example 14. After isolating the reaction product, the protective groups are removed in the following manner:

(a) splitting off of the trichloroacetyl groups in methanol with 4 N KOH;

(b) splitting off of the o-nitrophenylsulphenyl groups with 2-mercaptobenzthiazole/HCl in methanol/methylene chloride; and (c) splitting off of the cyclohexylidene group by leaving the acid reaction solution to stand at room temperature.

After treatment with Lewatit MP 500 (OH$^-$) and purification by chromatography, 12 mg of product of $R_f$ value of 0.31 are obtained.

EXAMPLE 31

1-N-{2-[(S)-2,3-Dihydroxypropylamino]-ethoxycarbonyl}-sisomicin (a) 1,2-5,6-Dicyclohexylidene-mannitol 270 g of $ZnCl_2$ (fused and ground) are added in portions to 1.35 liters of cyclohexanone (dried over $K_2CO_3$ and distilled) in the course of about 30–60 minutes, the temperature remaining between 25° and 40°. This $ZnCl_2$ solution is added to 170 g (0.93 mol) of mannitol, with exclusion of moisture, and the mixture is stirred at 35°–37° for 90 minutes until the mannitol has dissolved. The reaction mixture is then introduced rapidly, and with thorough stirring, into a prepared solution of 340 g of $K_2CO_3/340$ ml of water which is covered with 1.35 liters of ether, and after 30 minutes $ZnCO_3$ is filtered off, the filtrate is washed with ether and the product phase is concentrated in vacuo. 281 g of a waxy residue are obtained and are dissolved hot in 300 ml of toluene. This solution is filtered and, after cooling, 1 liter of petroleum ether is added to the filtrate and the gelatinous precipitate is filtered off (frit) and stirred with a further $3 \times 350$ ml of petroleum ether. After drying over liquid paraffin at 50° in vacuo, 188 g (59%) of dicyclohexylidene-mannitol are obtained; melting point: 101°–102°.

NMR ($CDCl_3$): $\delta = 1.56$ (s, broad; 20 cyclohexylidene-H), 2.93 (d, J=7 Hz; 20H) and 3.5–4.4 ppm (m; 8H).

(b) Cyclohexylidene-D-glyceraldehyde 55.4 g (0.16 mol) of 1,2-5,6-dicyclohexylidene-mannitol in 800 ml of acetone are added to 735 ml of a buffer solution (prepared from 6.8 g of $KH_2PO_4$ in 500 ml of water + 56 ml of 0.1 N NaOH; made up to 1 liter with water), the pH value is adjusted to 7–8 by adding 2 ml of 2 N NaOH, and 35.5 g (0.166 mol) of $NaIO_4$ are added at room temperature, whereupon the temperature rises to 31°. After 70 minutes, the mixture is concentrated in vacuo, the residue is taken up in 500 ml of water and the aqueous mixture is extracted with $7 \times 150$ ml of methylene chloride. 47.2 g (85%) of crude cyclohexylideneglyceraldehyde are obtained and, because of the tendency to polymerise, are reacted immediately. Distillation of 11.7 g of crude product gave 8 g of pure aldehyde of boiling point 102°/1 mm.

NMR ($CDCl_3$): $\delta = 1.62$ (s, broad; 10 cyclohexylidene-H), 3.95–4.55 (m; $-CH_2CH<$) and 9.77 ppm (d, J=2 Hz; CHO).

(c) D-2-(1,4-Dioxa-spiro[4,5]decan-2-yl-methylamino)-ethanol 102 g (1.68 mols) of aminoethanol are dissolved in 800 ml of methanol and the pH is adjusted to 7.1 with methanolic hydrochloric acid. After adding 47.2 g (0.27 mol) of cyclohexylidene-D-glyceraldehyde (pH drops to 4.3), 10.8 g (0.17 mol) of $NaBCNH_3$ are added (pH rises to 6.9–7.1). The mixture is subsequently stirred at room temperature for 3 hours and is left to stand overnight. The suspension is concentrated, the residue is dissolved in 500 ml of water and the solution is adjusted to pH 6 with 21 ml of dilute HCl (1:1) so that the non-basic constituents can be extracted with ether. The aqueous phase is then adjusted to pH 8.3 with 65 ml of 2 N NaOH and is extracted with $13 \times 150$ ml of methylene chloride and the methylene chloride extract is washed with water, dried with $Na_2SO_4$ and concentrated in vacuo. Yield: 36.6 g of an oil (63%). $R_f$ value: 0.57 (methylene chloride/methanol/17% strength $NH_3=15:2:0.1$).

(d)
D-N-(2-Nitrophenylsulphenyl)-2-(1,4-dioxa-spiro[4,5]decan-2-yl-methylamino)-ethanol A solution of 37.8 g (0.2 mol) of o-nitrophenylsulphenyl chloride in 190 ml of dioxane, and 144 ml of 2 N NaOH are simultaneously added to a solution of 42.4 g (0.2 mol) of D-2-(1,4-dioxa-spiro[4,5]-decan-2-yl-methylamino)-ethanol in 375 ml of dioxane, whilst monitoring the pH, such that the pH value remains greater than 8. Thereafter, the mixture is concentrated, the residue is taken up in 400 ml of methylene chloride and the methylene chloride mixture is washed with water, dried with $Na_2SO_4$ and concentrated in vacuo. 84 g of a crude produce are obtained and, for purification, the crude product was dissolved in toluene and the solution was filtered over a column containing 1.7 kg of silica gel. The eluting agents used were (a) toluene, for washing out nonpolar impurities, and (b) toluene/ethyl acetate mixtures with an increasing ethyl acetate content (9:1)→(8:2)→(7:3). Yield: 65.1 g (88%) of an orange oil; $R_f$ value: 0.3 (toluene/ethyl acetate=2:1).

NMR (CDCl$_3$): $\delta=1.4$ (s, broad; 10 cyclohexylidene-H), 3.1–4.7 (m, 9 aliphatic H, 1 OH) and 7.2–8.4 ppm (m, 4 aromatic H).

(e) D-(4-Nitrophenyl)
N-(2-nitrophenylsulphenyl)-2-(1,4dioxa-spiro[4,5]decan-2-yl-methylamino)-ethyl carbonate 50.2 g (0.136 mol) of the product from stage (d) are dissolved in 710 ml of absolute pyridine, and 27.5 g (0.137 mol) of chloroformic acid p-nitrophenyl ester are added in portions, whilst cooling with ice, such that the temperature remains at 20°–21°. The mixture is stirred at room temperature for 90 minutes and at 40° for 4 hours. About 4 g of undissolved chloroformic acid p-nitrophenyl ester are then filtered off, the filtrate is concentrated, the residue is dissolved in methylene chloride, the methylene chloride solution is washed three times with ice-water, dried with $Na_2SO_4$ and filtered and the filtrate is evaporated in vacuo. The residue (79.6 g) is dissolved in a little methylene chloride and filtered over 1.4 kg of silica gel, using methylene chloride as the eluting agent. Yield: 37 g (51%) of an orange oil; $R_f$ value: 0.4 (methylene chloride). NMR (CDCl$_3$): $\delta=1.6$ (s, broad; 10 cyclohexylidene-H), 3.2–4.7 (m, 9 aliphatic H) and 7.2–8.5 ppm (m with the AB system of the 4-nitrophenyl ester; 8 aromatic H).

(f)
1-N-{2-[(S)-2,3-Dihydroxypropylamino]-ethoxycarbonyl)}-sisomicin 20.7 g ($3.9\times10^{-2}$ mol) of stage (e) are added to a solution of 39 g (72% strength, $3.7\times10^{-2}$ mol) of the product from Example 5 in 200 ml of pyridine at room temperature and the mixture is left to stand overnight. It is evaporated under a high vacuum (62.3 g of an orange oil) and the residue is filtered over a column containing 500 g of silica gel, 4-nitrophenol and some impurities being eluted with (a) methylene chloride and successively, the reaction product being eluted with (b) methylene chloride/methanol/20% strength $NH_3$ (930:65:5). 38 g of an orange foam are thus obtained and, to split off the trichloroacetyl groups, this foam is dissolved in 785 ml of methanol, 250 ml of 4 N KOH are added and the mixture is left to stand overnight at room temperature. The alkaline solution is concentrated down to 100 ml in vacuo and the aqueous phase is decanted off from the undissolved orange residue, the residue being taken up in methylene chloride and the methylene chloride mixture being washed with water until neutral. After drying the mixture with $Na_2SO_4$ and concentrating it, 23 g of an intermediate product are isolated and are taken up in 60 ml of methylene chloride, a solution of 35.5 g (0.21 mol) of 2-mercaptobenzthiazole in 125 ml of methanol/120 ml of methylene chloride is added and the mixture is acidified with aqueous HCl (1:1) until the colour changes to yellow. The sisomicin derivative is extracted with $2\times150$ ml of water, the aqueous phase is washed with $3\times50$ ml of $CH_2Cl_2$, the acid solution is left to stand at room temperature for 2 days, in order to split off the cyclohexylidene group, and is then rendered basic with Lewatit MP 500 (OH$^-$) and concentrated in vacuo. Yield: 16 g of a crude product, from which 11.4 g (51%) of pure sisomicin derivative was obtained after purification by chromatography on silica gel using methylene chloride/methanol/20% strength $NH_3$ (2:4:1) as the eluting agent. $R_f$ value: 0.31 (sisomicin: 0.26). $^{13}$C-NMR (D$_2$O/dioxane): $\delta=52.08$ (C-1); 35.62 (C-2); 51.52 (C-3); 84.59 (C-4); 75.61 (C-5); 81.78 (C-6); 158.71 (CO); 68.27 (CH$_2$, $\alpha$ to COO); 48.04 (CH$_2\beta$ to COO); 49.85 (CH$_2$, $\alpha$ to NH); 71.25 (CHOH); and 64.93 (CH$_2$OH) ppm.

EXAMPLE 32

1-N-[2-(2,3-Dihydroxypropylamino)-ethoxycarbonyl]-sisomicin (a)
D,L-2-(1,4-Dioxa-spiro[4,5]decan-2-yl-methylamino)-ethanol 38 g (0.2 mol) of 2-chloromethyl-1,4-dioxaspiro[4,5]decane (German Auslegeschrift (German Published Specification) 1,593,797) in 150 ml of aminoethanol are heated under reflux with 50 g of anhydrous ground $Na_2CO_3$ for 18 hours. The undissolved salt is filtered off over a frit, excess aminoethanol is distilled off in vacuo and the residue is stirred with methylene chloride and filtered off again. After concentrating the filtrate, an oil is obtained, and was filtered over 220 g of silica gel to separate off the strongly polar aminoethanol residue (methylene chloride/methanol/17% strength $NH_3=15:2:0.1$ as the eluting agent). Yield: 32 g (74%) of an oil.

A yield of 52% is achieved on purification by distillation (boiling point: 145° C./1.3 mm). $R_f$ value: 0.57 (methylene chloride/methanol/17% strength $NH_3=15:2:0.1$).

(b)
1-N-[2-(2,3-Dihydroxypropylamino)-ethoxycarbonyl]-sisomicin

The procedure followed is as in Example 31, stages (d)–(f), and the sisomicin derivative is isolated, with the same $R_f$ value, in a yield of 48%.

EXAMPLE 33

1-N-{2-[(S)-2,3-Cyclohexylidenedioxypropylamino]-ethoxycarbonyl}-sisomicin

The procedure followed is as in Example 31 f, with the difference that after splitting off the o-nitrophenylsulphenyl groups with 2-mercaptobenzthiazole/HCl, the mixture is immediately rendered basic with Lewatit MP 500 (OH⁻) in order to avoid hydrolysis of the cyclohexylidene group. The mixture is then concentrated and the residue is purified by chromatography. $R_f$ value: 0.71 (methylene chloride/methanol 20% strength $NH_3 = 2:4:1$). $^{13}C$-NMR ($D_2O$: $\delta = 51.45$ (C-1); 31.86 (C-2); 51.16 (C-3); 81.22 (C-4); 74.75 (C-5); 80.96 (C-6); 157.59 (CO); 61.50 ($CH_2$, α to COO); 47.26 ($CH_2$, β to COO); 49.66 ($CH_2$ α to NH); 66.99 (CH-O), 66.90 ($CH_2O$); 112.71 (C-1 of the cyclo hexylidene radical); 34.61 and 35.86 (C-2 and C-6 of the cyclohexylidene radical); 24.14 and 24.40 (C-3 and C-5 of the cyclohexylidene radical); and 23.88 (C-4 of the cyclohexylidene radical) ppm.

EXAMPLE 34

1-N-{2-[(S)-2,3-Isopropylidenedioxypropylamino]-ethoxycarbonyl}-sisomicin (a) D-2-(2,3-Isopropylidenedioxypropylamino)-ethanol The procedure followed is analogous to Example 31 (c), isopropylidene-D-glyceraldehyde being used for the reductive alkylation. Yield: 62%; $R_f$ value: 0.45 (methylene chloride/methanol/17% strength $NH_3 = 15:2:0.1$)

(b) D-N-(o-nitrophenylsulphenyl)-2-(2,3-isopropylidenedioxypropylamino)-ethanol

The procedure followed is analogous to Example 31 (d), the produce from Example 34 (a) being used as the starting material. Yield: 79%, (c) D-(4-nitrophenyl) N-(o-nitrophenylsulphenyl)-2-(2,3-isopropylidenedioxypropylamino)-ethyl carbonate The procedure followed is as in Example 31 (e), the produce from Example 34 (b) being used. Yield: 55%, (d) 1-N-{2-[(S)-2,3-Isopropylidenedioxypropylamino]-ethoxycarbonyl}-sisomicin The procedure followed is as according to Example 33, using the product from Example 34 (c) as the acylating agent. $R_f$ value: 0.69.

The present invention also comprises pharmaceutically acceptable bioprecursors of the active compounds of the present invention.

For the purposes of this specification the term 'pharmaceutically acceptable bioprecursors' of an active compound of the invention means a compound having a structural formula different from the active compound but which nonetheless, upon administration to a warm-blooded animal is converted in the subject's body to the active compound.

What is claimed is:

1. A sisomicin derivative of the formula

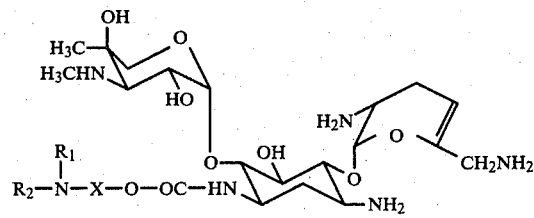

(I)

or a pharmaceutically acceptable salt thereof, in which
X denotes a straight-chain, branched or cyclic saturated or unsaturated aliphatic radical with 2 to 10 carbon atoms,
$R_1$ denotes a hydrogen atom or a $C_1$ to $C_4$ alkyl or benzyl radical and
$R_2$ denotes a radical of the general formula

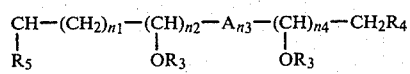

in which
A denotes

—CH=CH— or [—$CH_{(2-n5)}(CH_2OR_3)_{n5}$]

$R_3$ denotes a hydrogen atom or triphenylmethyl, $C_1$–$C_4$-alkyl, $C_2$–$C_4$-alkylcarbonyl, formyl or benzoyl, or 2 radicals $R_3$ together denote an alkylidene radical,
$R_4$ denotes a hydrogen atom or a $OR_3$ group, (in which $R_3$ has the above-mentioned meaning)
$R_5$ denotes a hydrogen atom or a $C_1$ to $C_4$ alkyl group which is unsubstituted or substituted by 1 to 3 hydroxyl groups,
$n_1$ is 0, 1, 2 or 3,
$n_2$ is 0, 1, 2, 3, 4 or 5 and
$n_3$, $n_4$ and $n_5$ independently of one another are 0, 1 or 2,
the sum of $n_1$, $n_2$, $n_3$ and $n_4$ is 1, 2, 3, 4 or 5 and the total number of $OR_3$ groups is 1 to 6.

2. A compound according to claim 1 in which X denotes a $C_2$ to $C_6$ alkylene radical and $R_1$ denotes a hydrogen atom.

3. Compounds according to claim 1, in which $R_3$ denotes a hydrogen atom.

4. A pharmaceutical composition containing as an active ingredient an antibacterially effective amount of a compound according to claim 1 in admixture with a liquid diluent.

5. A pharmaceutical composition of claim 4 in the form of a sterile or physiologically isotonic aqueous solution.

6. A topical composition according to claim 4 containing from 0.1 to 3.0 g of the said active ingredient, per 100 g of ointment, cream or lotion.

7. A medicament in dosage unit form comprising a compound according to claim 1 together with an inert pharmaceutical carrier.

8. A medicament of claim 7 in the form of tablets, pills, dragees, capsules, ampoules, or suppositories.

9. A method of combating bacterial infections in warm-blooded animals which comprises administering to the animals an antibacterially effective amount of an active compound according to claim 1 either alone or in admixture with a diluent or in the form of a medicament.

10. A method according to claim 9 in which the active compound is administered in an amount of 100 to 500 mg per day.

11. A compound according to claim 1 which is 1-N-[2-(1,3-Dihydroxypropyl-2-amino)-ethoxycarbonyl]-sisomicin.

12. A compound according to claim 1 which is 1-N-{2-[(S)-2,3-Dihydroxypropylamino]-ethoxycarbonyl}-sisomicin.

13. A compound according to claim 1 which is 1-N-[2-(1-Hydroxypropyl-2-amino)-ethoxycarbonyl]-sisomicin.

14. A compound according to claim 1 which is 1-N-{2-[(S,R)-2,3,4-Trihydroxybutylamino]-ethoxycarbonyl}-sisomicin.

15. A compound according to claim 1 which is 1-N-{2-[(S,S,R)-2,3,4,5-Tetrahydroxypentylamino]-ethoxycarbonyl}-sisomicin.

16. A compound according to claim 1 which is 1-N-{3-[(S)-2,3-Dihydroxypropylamino]-propoxycarbonyl}-sisomicin.

17. A compound according to claim 1 which is 1-N-{6-[(S)-2,3-Dihydroxypropylamino]-hexyloxycarbonyl}-sisomicin.

18. A compound according to claim 1 which is 1-N-[3-(1,3-Dihydroxyprop-2-ylamino)-propoxycarbonyl]-sisomicin.

* * * * *